United States Patent [19]

Bundy

[11] 4,230,629
[45] * Oct. 28, 1980

[54] 16-PHENOXY-9-DEOXY-9-METHYLENE-PGF COMPOUNDS

[75] Inventor: Gordon L. Bundy, Portage, Mich.

[73] Assignee: The Upjohn Company, Kalamazoo, Mich.

[*] Notice: The portion of the term of this patent subsequent to Oct. 10, 1995, has been disclaimed.

[21] Appl. No.: 941,095

[22] Filed: Sep. 8, 1978

Related U.S. Application Data

[60] Division of Ser. No. 832,242, Sep. 12, 1977, Pat. No. 4,119,649, which is a division of Ser. No. 682,848, May 4, 1976, Pat. No. 4,060,534, which is a continuation-in-part of Ser. No. 651,622, Jan. 23, 1976, Pat. No. 4,021,467, which is a division of Ser. No. 556,768, Mar. 10, 1975, Pat. No. 3,950,363.

[51] Int. Cl.$^3$ ............................ C09F 5/00; C09F 7/00; C11C 3/00

[52] U.S. Cl. .................................... 260/404; 260/408; 260/410; 260/410.5; 260/410.9 R; 260/413; 560/60; 562/465; 562/470

[58] Field of Search ................... 260/404, 408, 501.16, 260/501.18, 410 P, 410.5, 410.9 P, 413 P; 560/60; 562/465, 470

[56] References Cited

U.S. PATENT DOCUMENTS

| 3,931,299 | 1/1976 | Strike | 260/514 D |
| 4,119,649 | 10/1969 | Bundy | 260/408 |

Primary Examiner—John F. Niebling
Attorney, Agent, or Firm—Robert A. Armitage

[57] ABSTRACT

The present invention provides novel 16-phenoxy-9-deoxy-9-methylene-PGF-type compounds, exhibiting pharmacological properties comparable to the corresponding prostaglandin E-type compounds.

187 Claims, No Drawings

16-PHENOXY-9-DEOXY-9-METHYLENE-PGF COMPOUNDS

CROSS REFERENCE TO RELATED APPLICATIONS

The present application is a divisional application of U.S. Ser. No. 832,242, filed Sept. 12, 1977, now issued as U.S. Pat. No. 4,119,649, which is a divisional application of U.S. Ser. No. 682,848, filed May 4, 1976, now issued as U.S. Pat. No. 4,060,534 on Nov. 29, 1977; which is a continuation-in-part of U.S. Ser. No. 651,622, filed Jan. 23, 1976, now issued as U.S. Pat. No. 4,021,467 on May 3, 1977; which is a division of U.S. Ser. No. 556,768, filed Mar. 10, 1975, now issued as U.S. Pat. No. 3,950,363 on Apr. 13, 1976.

The present invention provides novel prostaglandin analogs, namely novel 16-phenoxy-9-deoxy-9-methylene-PGF type compounds, for which the essential material constituting a disclosure of their preparation and use is incorporated here by reference from U.S. Pat. No. 4,060,534, issued Nov. 29, 1977. As described in U.S. Pat. No. 4,060,534, the novel prostaglandin analogs of the present invention are useful for the same pharmacological purposes as the corresponding prostaglandin E-type compounds.

I claim:

1. A prostaglandin analog of the formula

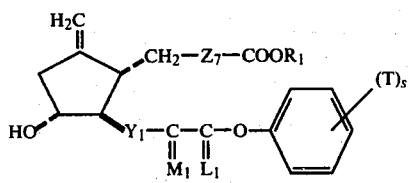

wherein $Y_1$ is trans-CH=CH—, —C≡C—, or —CH$_2$CH$_2$—;

wherein s is zero, one, two or 3, and T is chloro, fluoro, trifluoromethyl, alkyl of one to 3 carbon atoms, inclusive, or alkoxy of one to three carbon atoms, inclusive, with the proviso that not more than two T's are other than alkyl, the various T's being the same or different;

wherein $M_1$ is

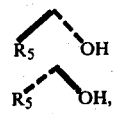

wherein $R_5$ is hydrogen or methyl;
wherein $L_1$ is

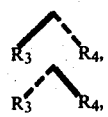

or a mixture of

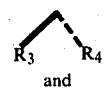

wherein $R_3$ and $R_4$ are hydrogen or methyl, being the same or different; and
wherein $Z_7$ is
(1) cis-CH=CH—CH$_2$—(CH$_2$)$_g$—CH$_2$—,
(2) cis-CH=CH—CH$_2$—(CH$_2$)$_g$—CF$_2$—,
(3) cis-CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—, and
(8) —CH$_2$—C≡C—(CH$_2$)$_g$—CH$_2$—,
wherein g is one, 2, or 3; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A prostaglandin analog according to claim 1, wherein $Y_1$ is —CH$_2$CH$_2$—.

3. A prostaglandin analog according to claim 2, wherein $Z_7$ is cis-CH=CH—CH$_2$—(CH$_2$)$_g$—CF$_2$—.

4. 9-Deoxy-9-methylene-2,2-difluoro-13,14-dihydro-16-phenoxy-17,18,19,20-tetranor-PGF$_2$, a prostaglandin analog according to claim 3.

5. A prostaglandin analog according to claim 1, wherein $Z_7$ is —(CH$_2$)$_3$—(CH$_2$)$_g$—CF$_2$—.

6. 9-Deoxy-9-methylene-2,2-difluoro-13,14-dihydro-16-phenoxy-17,18,19,20-tetranor-PGF$_1$, a prostaglandin analog according to claim 5.

7. A prostaglandin analog according to claim 1, wherein $Z_7$ is cis-CH$_2$—CH=CH—(CH$_2$)$_g$—CH$_2$—.

8. 9-Deoxy-9-methylene-cis-4,5-didehydro-13,14-dihydro-16-phenoxy-17,18,19,20-tetranor-PGF$_1$, a prostaglandin analog according to claim 7.

9. A prostaglandin analog according to claim 2, wherein $Z_7$ is —CH$_2$—O—CH$_2$—(CH$_2$)$_g$—CH$_2$—.

10. 9-Deoxy-9-methylene-5-oxa-13,14-dihydro-16-phenoxy-17,18,19,20-tetranor-PGF$_1$, a prostaglandin analog according to claim 9.

11. A prostaglandin analog according to claim 2, wherein $Z_7$ is —CH$_2$—C≡C—(CH$_2$)$_g$—CH$_2$—.

12. 9-Deoxy-9-methylene-5,6-didehydro-13,14-dihydro-16-phenoxy-17,18,19,20-tetranor-PGF$_2$, a prostaglandin analog according to claim 11.

13. A prostaglandin analog according to claim 2, wherein $Z_7$ is —CH$_2$—C≡C—(CH$_2$)$_g$—CH$_2$—.

14. 9-Deoxy-9-methylene-4,4,5,5-tetradehydro-13,14-dihydro-16-phenoxy-17,18,19,20-tetranor-PGF$_1$, a prostaglandin analog according to claim 13.

15. A prostaglandin analog according to claim 2, wherein $Z_7$ is —(CH$_2$)$_3$—(CH$_2$)$_g$—CH$_2$13.

16. A prostaglandin analog according to claim 15, wherein $M_1$ is

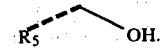

17. 9-Deoxy-9-methylene-15-epi-13,14-dihydro-16-phenoxy-17,18,19,20-tetranor-PGF$_1$, a prostaglandin analog according to claim 16.

18. A prostaglandin analog according to claim 15, wherein $M_1$ is

19. A prostaglandin analog according to claim 18, wherein s is zero or one, and T is chloro, fluoro, or trifluoromethyl.

20. A prostaglandin analog according to claim 19, wherein g is 3.

21. 9-Deoxy-9-methylene-2a,2b-dihomo-15-methyl-13,14-dihydro-16-phenoxy-17,18,19,20-tetranor-PGF$_1$, a prostaglandin analog according to claim 20.

22. 9-Deoxy-9-methylene-2a,2b-dihomo-13,14-dihydro-16-phenoxy-17,18,19,20-tetranor-PGF$_1$, a prostaglandin analog according to claim 20.

23. A prostaglandin analog according to claim 19, wherein g is one.

24. A prostaglandin analog according to claim 23, wherein at least one of $R_3$ and $R_4$ is methyl.

25. A prostaglandin analog according to claim 24, wherein $R_3$ and $R_4$ are both methyl.

26. 9-Deoxy-9-methylene-16-methyl-13,14-dihydro-16-phenoxy-18,19,20-trinor-PGF$_1$, a prostaglandin analog according to claim 25.

27. A prostaglandin analog according to claim 23, wherein $R_3$ and $R_4$ are both hydrogen.

28. A prostaglandin analog according to claim 27, wherein $R_5$ is methyl.

29. 9-Deoxy-9-methylene-15-methyl-13,14-dihydro-16-phenoxy-17,18,19,20-tetranor-PGF$_1$, a prostaglandin analog according to claim 28.

30. A prostaglandin analog according to claim 27, wherein $R_5$ is hydrogen.

31. 9-Deoxy-9-methylene-13,14-dihydro-16-phenoxy-17,18,19,20-tetranor-PGF$_1$, a prostaglandin analog according to claim 30.

32. A prostaglandin analog according to claim 2, wherein $Z_7$ is cis-CH=CH—CH$_2$—(CH$_2$)$_g$—CH$_2$—.

33. A prostaglandin analog according to claim 32, wherein $M_1$ is

34. A prostaglandin analog according to claim 33, wherein s is zero or one, and T is chloro, fluoro, or trifluoromethyl.

35. A prostaglandin analog according to claim 34, wherein g is 3.

36. 9-Deoxy-9-methylene-2a,2b-dihomo-15-epi-15-methyl-13,14-dihydro-16-phenoxy-17,18,19,20-tetranor-PGF$_2$, a prostaglandin analog according to claim 35.

37. 9-Deoxy-9-methylene-2a,2b-dihomo-15-epi-13,14-dihydro-16-phenoxy-17,18,19,20-tetranor-PGF$_2$, a prostaglandin analog according to claim 35.

38. A prostaglandin analog according to claim 34, wherein g is one.

39. A prostaglandin analog according to claim 38, wherein at least one of $R_3$ and $R_4$ is methyl.

40. 9-Deoxy-9-methylene-15-epi-16-methyl-13,14-dihydro-16-phenoxy-18,19,20-trinor-PGF$_2$, a prostaglandin analog according to claim 39.

41. A prostaglandin analog according to claim 38, wherein $R_3$ and $R_4$ are both hydrogen.

42. 9-Deoxy-9-methylene-15-epi-15-methyl-13,14-dihydro-16-phenoxy-17,18,19,20-tetranor-PGF$_2$, a prostaglandin analog according to claim 41.

43. A prostaglandin analog according to claim 32, wherein $M_1$ is

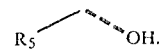

44. A prostaglandin analog according to claim 43, wherein s is zero or one, and T is chloro, fluoro or trifluoromethyl.

45. A prostaglandin analog according to claim 44, wherein g is 3.

46. A prostaglandin analog according to claim 45, wherein at least one of $R_3$ and $R_4$ is methyl.

47. 9-Deoxy-9-methylene-2a,2b-dihomo-16-methyl-13,14-dihydro-16-phenoxy-18,19,20-trinor-PGF$_2$, a prostaglandin analog according to claim 46.

48. A prostaglandin analog according to claim 45, wherein $R_3$ and $R_4$ are both hydrogen.

49. 9-Deoxy-9-methylene-2a,2b-dihomo-15-methyl-13,14-dihydro-16-phenoxy-17,18,19,20-tetranor-PGF$_2$, a prostaglandin analog according to claim 48.

50. A prostaglandin analog according to claim 44, wherein g is one.

51. A prostaglandin analog according to claim 50, wherein at least one of $R_3$ and $R_4$ is methyl.

52. A prostaglandin analog according to claim 51, wherein $R_3$ and $R_4$ are both methyl.

53. 9-Deoxy-9-methylene-16-methyl-13,14-dihydro-16-phenoxy-18,19,20-trinor-PGF$_2$, tris-(hydroxymethyl)-aminomethane salt, a prostaglandin analog according to claim 52.

54. 9-Deoxy-9-methylene-16-methyl-13,14-dihydro-16-phenoxy-18,19,20-trinor-PGF$_2$, methyl ester, a prostaglandin analog according to claim 52.

55. 9-Deoxy-9-methylene-16-methyl-13,14-dihydro-16-phenoxy-18,19,20-trinor-PGF$_2$, a prostaglandin analog according to claim 52.

56. A prostaglandin analog according to claim 50, wherein $R_3$ and $R_4$ are both hydrogen.

57. A prostaglandin analog according to claim 56, wherein $R_5$ is methyl.

58. 9-Deoxy-9-methylene-15-methyl-13,14-dihydro-16-phenoxy-17,18,19,20-tetranor-PGF$_2$, tris-(hydroxymethyl)-aminomethane salt, a prostaglandin analog according to claim 57.

59. 9-Deoxy-9-methylene-15-methyl-13,14-dihydro-16-phenoxy-17,18,19,20-tetranor-PGF$_2$, methyl ester, a prostaglandin analog according to claim 57.

60. 9-Deoxy-9-methylene-15-methyl-13,14-dihydro-16-phenoxy-17,18,19,20-tetranor-PGF$_2$, a prostaglandin analog according to claim 57.

61. A prostaglandin analog according to claim 56, wherein $R_5$ is hydrogen.

62. 9-Deoxy-9-methylene-13,14-dihydro-16-phenoxy-17,18,19,20-tetranor-PGF$_2$, a methyl ester, a prostaglandin analog according to claim 61.

63. 9-Deoxy-9-methylene-13,14-dihydro-16-phenoxy-17,18,19,20-tetranor-PGF$_2$, a prostaglandin analog according to claim 61.

64. A prostaglandin analog according to claim 1, wherein $Y_1$ is —C≡C—.

65. A prostaglandin analog according to claim 64, wherein $Z_7$ is cis-CH=CH—CH$_2$—(CH$_2$)$_g$—CF$_2$—.

66. 9-Deoxy-9-methylene-2,2-difluoro-13,14-didehydro-16-phenoxy-17,18,19,20-tetranor-PGF$_2$, a prostaglandin analog according to claim 65.

67. A prostaglandin analog according to claim 64, wherein Z$_7$ is —(CH$_2$)$_3$—(CH$_2$)$_g$—CF$_2$—.

68. 9-Deoxy-9-methylene-2,2-difluoro-13,14-didehydro-16-phenoxy-17,18,19,20-tetranor-PGF$_1$, a prostaglandin analog according to claim 67.

69. A prostaglandin analog according to claim 64, wherein Z$_7$ is cis-CH$_2$—CH=CH—(CH$_2$)$_g$—CH$_2$—.

70. 9-Deoxy-9-methylene-cis-4,5-didehydro-13,14-didehydro-16-phenoxy-17,18,19,20-tetranor-PGF$_1$, a prostaglandin analog according to claim 69.

71. A prostaglandin analog according to claim 64, wherein Z$_7$ is —CH$_2$—O—CH$_2$—(CH$_2$)$_g$—CH$_2$—.

72. 9-Deoxy-9-methylene-5-oxa-13,14-didehydro-16-phenoxy-17,18,19,20-tetranor-PGF$_1$, a prostaglandin analog according to claim 71.

73. A prostaglandin analog according to claim 64, wherein Z$_7$ is —C≡C—CH$_2$—(CH$_2$)$_g$—CH$_2$—.

74. 9-Deoxy-9-methylene-5,6,13,14-tetradehydro-16-phenoxy-17,18,19,20-tetranor-PGF$_2$, a prostaglandin analog according to claim 73.

75. A prostaglandin analog according to claim 64, wherein Z$_7$ is —CH$_2$—C≡C—(CH$_2$)$_g$—CH$_2$—.

76. 9-Deoxy-9-methylene-4,4,5,5,13,14-hexadehydro-16-phenoxy-17,18,19,20-tetranor-PGF$_1$, a prostaglandin analog according to claim 75.

77. A prostaglandin analog according to claim 64, wherein Z$_7$ is —(CH$_2$)$_3$—(CH$_2$)$_g$—CH$_2$—.

78. A prostaglandin analog according to claim 77, wherein M$_1$ is

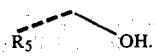

79. 9-Deoxy-9-methylene-15-epi-13,14-didehydro-16-phenoxy-17,18,19,20-tetranor-PGF$_1$, a prostaglandin analog according to claim 78.

80. A prostaglandin analog according to claim 77, wherein M$_1$ is

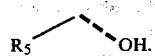

81. A prostaglandin analog according to claim 80, wherein s is zero or one, and T is chloro, fluoro or trifluoromethyl.

82. A prostaglandin analog according to claim 81, wherein g is 3.

83. 9-Deoxy-9-methylene-2a,2b-dihomo-15-methyl-13,14-didehydro-16-phenoxy-17,18,19,20-tetranor-PGF$_1$, a prostaglandin analog according to claim 82.

84. 9-Deoxy-9-methylene-2a,2b-dihomo-13,14-didehydro-16-phenoxy-17,18,19,20-tetranor-PGF$_1$, a prostaglandin analog according to claim 82.

85. A prostaglandin analog according to claim 81, wherein g is one.

86. A prostaglandin analog according to claim 85, wherein at least one of R$_3$ and R$_4$ is methyl.

87. A prostaglandin analog according to claim 86, wherein R$_3$ and R$_4$ are both methyl.

88. 9-Deoxy-9-methylene-16-methyl-13,14-didehydro-16-phenoxy-18,19,20-trinor-PGF$_1$, a prostaglandin analog according to claim 82.

89. A prostaglandin analog according to claim 85, wherein R$_3$ and R$_4$ are both hydrogen.

90. A prostaglandin analog according to claim 89, wherein R$_5$ is methyl.

91. 9-Deoxy-9-methylene-15-methyl-13,14-didehydro-16-phenoxy-17,18,19,20-tetranor-PGF$_1$, a prostaglandin analog according to claim 90.

92. A prostaglandin analog according to claim 89, wherein R$_5$ is hydrogen.

93. 9-Deoxy-9-methylene-13,14-didehydro-16-phenoxy-17,18,19,20-tetranor-PGF$_1$, a prostaglandin analog according to claim 92.

94. A prostaglandin analog according to claim 64, wherein Z$_7$ is cis-CH=CH—CH$_2$—(CH$_2$)$_g$—CH$_2$—.

95. A prostaglandin analog according to claim 94, wherein M$_1$ is

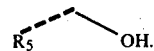

96. A prostaglandin analog according to claim 95, wherein s is zero or one, and T is chloro, fluoro or trifluoromethyl.

97. A prostaglandin analog according to claim 96, wherein g is 3.

98. 9-Deoxy-9-methylene-2a,2b-dihomo-15-epi-15-methyl-13,14-didehydro-16-phenoxy-17,18,19,20-tetranor-PGF$_2$, a prostaglandin analog according to claim 96.

99. 9-Deoxy-9-methylene-2a,2b-dihomo-15-epi-13,14-didehydro-16-phenoxy-17,18,19,20-tetranor-PGF$_2$, a prostaglandin analog according to claim 97.

100. A prostaglandin analog according to claim 96, wherein g is one.

101. A prostaglandin analog according to claim 100, wherein at least one of R$_3$ and R$_4$ is methyl.

102. 9-Deoxy-9-methylene-15-epi-16-methyl-13,14-didehydro-16-phenoxy-18,19,20-trinor-PGF$_2$, a prostaglandin analog according to claim 101.

103. A prostaglandin analog according to claim 100, wherein R$_3$ and R$_4$ are both hydrogen.

104. 9-Deoxy-9-methylene-15-epi-15-methyl-13,14-didehydro-16-phenoxy-17,18,19,20-tetranor-PGF$_2$, a prostaglandin analog according to claim 103.

105. A prostaglandin analog according to claim 94, wherein M$_1$ is

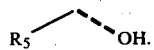

106. A prostaglandin analog according to claim 105, wherein s is zero or one, and T is chloro, fluoro or trifluoromethyl.

107. A prostaglandin analog according to claim 106, wherein g is 3.

108. A prostaglandin analog according to claim 107, wherein at least one of R$_3$ and R$_4$ is methyl.

109. 9-Deoxy-9-methylene-2a,2b-dihomo-16-methyl-13,14-didehydro-16-phenoxy-18,19,20-trinor-PGF$_2$, a prostaglandin analog according to claim 108.

110. A prostaglandin analog according to claim 106, wherein R$_3$ and R$_4$ are both hydrogen.

111. 9-Deoxy-9-methylene-2a,2b-dihomo-15-methyl-13,14-didehydro-16-phenoxy-17,18,19,20-tetranor-PGF$_2$, a prostaglandin analog according to claim 110.

112. A prostaglandin analog according to claim 106, wherein g is one.

113. A prostaglandin analog according to claim 112, wherein at least one of R₃ and R₄ is methyl.

114. A prostaglandin analog according to claim 113, wherein R₃ and R₄ are both methyl.

115. 9-Deoxy-9-methylene-16-methyl-13,14-didehydro-16-phenoxy-18,19,20-trinor-PGF₂, tris-(hydroxymethyl)-aminomethane salt, a prostaglandin analog according to claim 114.

116. 9-Deoxy-9-methylene-16-methyl-13,14-didehydro-16-phenoxy-18,19,20-trinor-PGF₂, methyl ester, a prostaglandin analog according to claim 114.

117. 9-Deoxy-9-methylene-16-methyl-13,14-didehydro-16-phenoxy-18,19,20-trinor-PGF₂, a prostaglandin analog according to claim 114.

118. A prostaglandin analog according to claim 112, wherein R₃ and R₄ are both hydrogen.

119. A prostaglandin analog according to claim 118, wherein R₅ is methyl.

120. 9-Deoxy-9-methylene-15-methyl-13,14-didehydro-16-phenoxy-17,18,19,20-tetranor-PGF₂, tris-(hydroxymethyl)aminomethane salt, a prostaglandin analog according to claim 119.

121. 9-Deoxy-9-methylene-15-methyl-13,14-didehydro-16-phenoxy-17,18,19,20-tetranor-PGF₂, methyl ester, a prostaglandin analog according to claim 119.

122. 9-Deoxy-9-methylene-15-methyl-13,14-didehydro-16-phenoxy-17,18,19,20-tetranor-PGF₂, a prostaglandin analog according to claim 119.

123. A prostaglandin analog according to claim 118, wherein R₅ is hydrogen.

124. 9-Deoxy-9-methylene-13,14-didehydro-16-phenoxy-17,18,19,20-tetranor-PGF₂, methyl ester, a prostaglandin analog according to claim 123.

125. 9-Deoxy-9-methylene-13,14-didehydro-16-phenoxy-17,18,19,20-tetranor-PGF₂, a prostaglandin analog according to claim 123.

126. A prostaglandin analog according to claim 1, wherein Y₁ is trans-CH=CH—.

127. A prostaglandin analog according to claim 126, wherein Z₇ is cis-CH=CH—CH₂—(CH₂)$_g$—CF₂—.

128. 9-Deoxy-9-methylene-2,2-difluoro-16-phenoxy-17,18,19,20-tetranor-PGF₂, a prostaglandin analog according to claim 127.

129. A prostaglandin analog according to claim 126, wherein Z₇ is —(CH₂)₃—(CH₂)$_g$—CF₂—.

130. 9-Deoxy-9-methylene-2,2-difluoro-16-phenoxy-17,18,19,20-tetranor-PGF₁, a prostaglandin analog according to claim 129.

131. A prostaglandin analog according to claim 126, wherein Z₇ is cis-CH₂—CH=CH—(CH₂)$_g$—CH₂/—.

132. 9-Deoxy-9-methylene-cis-4,5-didehydro-16-phenoxy-17,18,19,20-tetranor-PGF₁, a prostaglandin analog according to claim 131.

133. A prostaglandin analog according to claim 126, wherein Z₇ is —CH₂—O—CH₂—(CH₂)$_g$—CH₂—.

134. 9-Deoxy-9-methylene-5-oxa-16-phenoxy-17,18,19,20-tetranor-PGF₁, a prostaglandin analog according to claim 133.

135. A prostaglandin analog according to claim 126, wherein Z₇ is —C≡C—CH₂—(CH₂)$_g$—CH₂—.

136. 9-Deoxy-9-methylene-5,6-didehydro-16-phenoxy-17,18,19,20-tetranor-PGF₂, a prostaglandin analog according to claim 135.

137. A prostaglandin analog according to claim 126, wherein Z₇ is —CH₂—C≡C—(CH₂)$_g$—CH₂—.

138. 9-Deoxy-9-methylene-4,4,5,5-tetradehydro-16-phenoxy-17,18,19,20-tetranor-PGF₁, a prostaglandin analog according to claim 137.

139. A prostaglandin analog according to claim 126, wherein Z₇ is —(CH₂)₃—(CH₂)$_g$—CH₂—.

140. A prostaglandin analog according to claim 139, wherein M₁ is

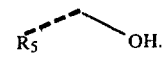

141. 9-Deoxy-9-methylene-15-epi-16-phenoxy-17,18,19,20-tetranor-PGF₁, a prostaglandin analog according to claim 140.

142. A prostaglandin analog according to claim 139, wherein M₁ is

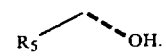

143. A prostaglandin analog according to claim 142, wherein s is zero or one, and T is chloro, fluoro or trifluoromethyl.

144. A prostaglandin analog according to claim 143, wherein g is 3.

145. 9-Deoxy-9-methylene-2a,2b-dihomo-15-methyl-16-phenoxy-17,18,19,20-tetranor-PGF₁, a prostaglandin analog according to claim 144.

146. 9-Deoxy-9-methylene-2a,2b-dihomo-16-phenoxy-17,18,19,20-tetranor-PGF₁, a prostaglandin analog according to claim 144.

147. A prostaglandin analog according to claim 143, wherein g is one.

148. A prostaglandin analog according to claim 147, wherein at least one of R₃ and R₄ is methyl.

149. A prostaglandin analog according to claim 148, wherein R₃ and R₄ are both methyl.

150. 9-Deoxy-9-methylene-16-phenoxy-18,19,20-trinor-PGF₁, a prostaglandin analog according to claim 149.

151. A prostaglandin analog according to claim 147, wherein R₃ and R₄ are both hydrogen.

152. A prostaglandin analog according to claim 151, wherein R₅ is methyl.

153. 9-Deoxy-9-methylene-15-methyl-16-phenoxy-17,18,19,20-tetranor-PGF₁, a prostaglandin analog according to claim 152.

154. A prostaglandin analog according to claim 151, wherein R₅ is hydrogen.

155. 9-Deoxy-9-methylene-16-phenoxy-17,18,19,20-tetranor-PGF₁, a prostaglandin analog according to claim 154.

156. A prostaglandin analog according to claim 126, wherein Z₇ is cis-CH=CH—CH₂—(CH₂)$_g$—CH₂—.

157. A prostaglandin analog according to claim 156, wherein M₁ is

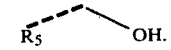

158. A prostaglandin analog according to claim 157, wherein s is zero or one, and T is chloro, fluoro or trifluoromethyl.

159. A prostaglandin analog according to claim 158, wherein g is 3.

160. 9-Deoxy-9-methylene-2a,2b-dihomo-15-epi-15-methyl-16phenoxy-17,18,19,20-tetranor-PGF$_2$, a prostaglandin analog according to claim 159.

161. 9-Deoxy-9-methylene-2a,2b-dihomo-15-epi-16-phenoxy-17,18,19,20-tetranor-PGF$_2$, a prostaglandin analog according to claim 159.

162. A prostaglandin analog according to claim 158, wherein g is one.

163. A prostaglandin analog according to claim 162, wherein at least one of R$_3$ and R$_4$ is methyl.

164. 9-Deoxy-9-methylene-15-epi-16-methyl-16-phenoxy-18,19,20-trinor-PGF$_2$, a prostaglandin analog according to claim 163.

165. A prostaglandin analog according to claim 162, wherein R$_3$ and R$_4$ are both hydrogen.

166. 9-Deoxy-9-methylene-15-epi-15 -methyl-16-phenoxy-17,18,19,20-tetranor-PGF$_2$, a prostaglandin analog according to claim 165.

167. A prostaglandin analog according to claim 156, wherein M$_1$ is

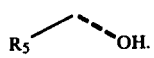

168. A prostaglandin analog according to claim 167, wherein s is zero or one, and T is chloro, fluoro or trifluoromethyl.

169. A prostaglandin analog according to claim 168, wherein g is 3.

170. A prostaglandin analog according to claim 169, wherein at least one of R$_3$ and R$_4$ is methyl.

171. 9-Deoxy-9-methylene-2a,2b-dihomo-16-methyl-16-phenoxy-18,19,20-trinor-PGF$_2$, a prostaglandin analog according to claim 101.

172. A prostaglandin analog according to claim 169, wherein R$_3$ and R$_4$ are both hydrogen.

173. 9-Deoxy-9-methylene-2a,2b-dihomo-15-methyl-16-phenoxy-17,18,19,20-tetranor-PGF$_2$, a prostaglandin analog according to claim 172.

174. A prostaglandin analog according to claim 168, wherein g is one.

175. A prostaglandin analog according to claim 174, wherein at least one of R$_3$ and R$_4$ is methyl.

176. A prostaglandin analog according to claim 175, wherein R$_3$ and R$_4$ are both methyl.

177. 9-Deoxy-9-methylene-16-methyl-16-phenoxy-18,19,20-trinor-PGF$_2$, tris-(hydroxymethyl)aminomethane salt, a prostaglandin analog according to claim 176.

178. 9-Deoxy-9-methylene-16-methyl-16-phenoxy-18,19,20-trinor-PGF$_2$, methyl ester, a prostaglandin analog according to claim 176.

179. 9-Deoxy-9-methylene-16-methyl-16-phenoxy-18,19,20-trinor-PGF$_2$, a prostaglandin analog according to claim 176.

180. A prostaglandin analog according to claim 174, wherein R$_3$ and R$_4$ are both hydrogen.

181. A prostaglandin analog according to claim 180, wherein R$_5$ is methyl.

182. 9-Deoxy-9-methylene-15-methyl-16-phenoxy-17,18,19,20-tetranor-PGF$_2$, tris-(hydroxymethyl)-aminomethane salt, a prostaglandin analog according to claim 181.

183. 9-Deoxy-9-methylene-15-methyl-16-phenoxy-17,18,19,20-tetranor-PGF$_2$, methyl ester, a prostaglandin analog according to claim 181.

184. 9-Deoxy-9-methylene-15-methyl-16-phenoxy-17,18,19,20-tetranor-PGF$_2$, a prostaglandin analog according to claim 181.

185. A prostaglandin analog according to claim 180, wherein R$_5$ is hydrogen.

186. 9-Deoxy-9-methylene-16-phenoxy-17,18,19,20-tetranor-PGF$_2$, methyl ester, a prostaglandin analog according to claim 185.

187. 9-Deoxy-9-methylene-16-phenoxy-17,18,19,20-tetranor-PGF$_2$, a prostaglandin analog according to claim 185.

* * * * *

UNITED STATES PATENT OFFICE
CERTIFICATE OF CORRECTION

Patent No. 4,230,629         Dated  28 October 1980

Inventor(s)  Gordon L. Bundy

It is certified that error appears in the above-identified patent and that said Letters Patent are hereby corrected as shown below:

Column 1, line 52, -- or -- should appear at line 52;
Column 2, line 32 and line 37, "according to claim 1" should read -- according to claim 2 --; line 58, "$-(CH_2)_3-(CH_2)_g-CH_2 13.$" should read -- $-(CH_2)_3-(CH_2)_g-CH_2-.$ --;
Column 5, line 68, "according to claim 82" should read -- according to claim 87 --;
Column 8, line 40, "9-Deoxy-9-methylene-16-phenoxy-" should read -- 9-Deoxy-9-methylene-16-methyl-16-phenoxy- --;

Signed and Sealed this

Fifth Day of May 1981

[SEAL]

Attest:

RENE D. TEGTMEYER

Attesting Officer    Acting Commissioner of Patents and Trademarks